(12) United States Patent
Uchida

(10) Patent No.: US 8,536,352 B2
(45) Date of Patent: Sep. 17, 2013

(54) METHOD OF PRODUCING EPOXY COMPOUNDS

(75) Inventor: Hiroshi Uchida, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 156 days.

(21) Appl. No.: 13/142,265

(22) PCT Filed: Dec. 17, 2009

(86) PCT No.: PCT/JP2009/071043
§ 371 (c)(1),
(2), (4) Date: Jun. 24, 2011

(87) PCT Pub. No.: WO2010/073960
PCT Pub. Date: Jul. 1, 2010

(65) Prior Publication Data
US 2011/0263882 A1    Oct. 27, 2011

(30) Foreign Application Priority Data

Dec. 26, 2008  (JP) ................ 2008-335187

(51) Int. Cl.
*C07D 301/12* (2006.01)

(52) U.S. Cl.
USPC ........................................ 549/531

(58) Field of Classification Search
USPC ................................ 549/525, 531
See application file for complete search history.

(56) References Cited

U.S. PATENT DOCUMENTS

| | | | |
|---|---|---|---|
| 5,578,740 A * | 11/1996 | Au et al. | 549/525 |
| 5,633,391 A | 5/1997 | Fenelli | |
| 7,074,947 B2 * | 7/2006 | Hirota et al. | 549/531 |
| 2005/0020841 A1 | 1/2005 | Hirota et al. | |

FOREIGN PATENT DOCUMENTS

| | | |
|---|---|---|
| JP | 58-173118 A | 10/1983 |
| JP | 60-060123 A | 4/1985 |
| JP | 04-275281 A | 9/1992 |
| JP | 07-145221 A | 6/1995 |
| JP | 10-511722 A | 11/1998 |
| JP | 2002-526483 A | 8/2002 |
| JP | 2003-300971 A | 10/2003 |
| JP | 2008/094741 A | 4/2008 |
| WO | 96/20232 A1 | 7/1996 |
| WO | 96/20233 A | 7/1996 |
| WO | 00/17178 A | 3/2000 |
| WO | 2009/107754 A1 | 9/2009 |

OTHER PUBLICATIONS

Supplementary European Search Report for Application No. 08934763.3-2101/2383264 dated Sep. 26, 2012.

C. Pac, T. Sakamoto: "Selective epoxidation of olefins by hydrogen peroxide in water using a polyoxometalate catalyst supported on chemically modified hydrophobic mesoporous silica gel", Tetrahedron Letters, vol. 41, 2000, pp. 10009-10012.

* cited by examiner

*Primary Examiner* — Taylor Victor Oh
(74) *Attorney, Agent, or Firm* — Sughrue Mion, PLLC

(57) ABSTRACT

Provided is a method of efficiently producing an epoxy compound from an allyl ether having an aromatic ring under mild conditions by using hydrogen peroxide as an oxidizing agent without using an organic solvent. The method of producing an epoxy compound comprises reacting an allyl ether having an aromatic ring with hydrogen peroxide to epoxidize a carbon-carbon double bond of an allyl group to thereby produce a corresponding epoxy compound having an aromatic ring, wherein water only is used as a solvent without using an organic solvent, and a tungsten compound, and a tertiary amine and/or a quaternary ammonium salt, are used as a reaction catalyst.

21 Claims, No Drawings

METHOD OF PRODUCING EPOXY COMPOUNDS

CROSS REFERENCE TO RELATED APPLICATIONS

This application is a National Stage of International Application No. PCT/JP2009/071043 filed Dec. 17, 2009, the contents of which are incorporated herein by reference in their entirety.

TECHNICAL FIELD

This invention relates to a method of producing epoxy compounds. More specifically, the invention relates to a method of producing epoxy compounds by efficiently epoxidizing an allyl group of an allyl ether having an aromatic ring.

BACKGROUND ART

An arylglycidyl ether, which is a known starting material of an epoxy resin, has been industrially produced on a large scale and has been widely used in a variety of fields.

A method of producing an arylglycidyl ether that has been conventionally known can be represented by a method of obtaining a glycidyl ether by reacting a corresponding phenol with epichlorohydrin in the presence or absence of a catalyst under a basic condition. In this method, remaining organic chlorine compounds result in disadvantageously decreasing an insulating property when used in some applications, such as in electronics.

Therefore, direct epoxidation of an allyl ether of phenol by using an oxidizing agent has been studied. Patent documents 1 (JP-T-10-511722) and 2 (JP-A-60-60123) disclose methods of epoxidizing a diallyl ether of bisphenol A or a polyallyl ether of a novolak type phenol resin with hydrogen peroxide in an organic solvent, such as toluene, by using sodium tungstate and a phosphoric acid catalyst in the presence of a quaternary ammonium salt. However, these methods cannot be industrially carried out, since the tungsten compound must be used in a very large amount, and the rate of epoxidation is not sufficient.

Patent document 3 (U.S. Pat. No. 5,633,391) discloses a method of epoxidizing an olefin by bringing the olefin into contact with bis(trimethylsilyl)peroxide as an oxidizing agent in an organic solvent in the presence of a rhenium oxide catalyst. However, an expensive catalyst and oxidizing agent are necessary, and yield is insufficient in the case of phenylallyl ether.

Patent documents 4 (JP-A-7-145221) and 5 (JP-A-58-173118) disclose methods of allyl-etherifying a phenol novolak resin with an allyl halide followed by epoxidation with a peracid in an organic solvent. However, a peracid, which is highly dangerous, should be used.

Further, patent document 6 (JP-T-2002-526483) discloses a method of epoxidation with hydrogen peroxide in the presence of a titanium-containing zeolite catalyst, and a tertiary amine, a tertiary amine oxide or a mixture thereof. However, though this method is useful for a substrate organic material having a small molecular weight, the catalytic efficiency is poor with respect to a substrate having large molecular weight, such as phenyl ether. Therefore, the method cannot be applied.

PRIOR ART DOCUMENTS

Patent Documents

Patent document 1: JP-T-10-511722
Patent document 2: JP-A-60-60123
Patent document 3: U.S. Pat. No. 5,633,391
Patent document 4: JP-A-7-145221
Patent document 5: JP-A-58-173118
Patent document 6: JP-T-2002-526483

SUMMARY OF THE INVENTION

Problems to be Solved by the Invention

The present invention is directed to a method of efficiently producing an epoxy compound from an allyl ether having an aromatic ring under mild conditions by using hydrogen peroxide as an oxidizing agent without using an organic solvent.

Means for Solving the Problems

Based on study in an effort to solve the above problems, the present inventor has found out that upon reacting an aqueous solution of hydrogen peroxide with allyl ethers having an aromatic ring without using an organic solvent but using as a catalyst a tungsten compound, and a tertiary organoamine and/or a quaternary ammonium salt, and optionally a mineral acid, a corresponding epoxy compound can be highly efficiently and selectively formed, and has completed the invention.

In particular, the present invention includes the following [1] to [11].

[1] A method of producing an epoxy compound by reacting an allyl ether having an aromatic ring with hydrogen peroxide to epoxidize a carbon-carbon double bond of an allyl group to thereby produce a corresponding epoxy compound having an aromatic ring, wherein water only is used as a solvent without using an organic solvent, and a tungsten compound, and a tertiary amine and/or a quaternary ammonium salt, are used as a reaction catalyst.

[2] The method described in [1] above, wherein the allyl ether having an aromatic ring has a structure represented by the following formula (1):

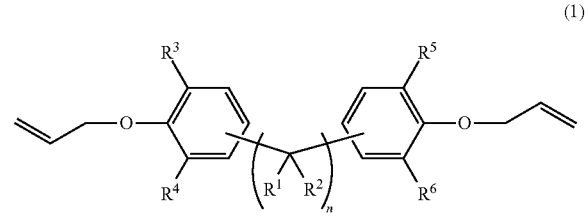

{wherein each of $R^1$ and $R^2$ is independently a hydrogen atom, an alkyl group having 1 to 6 carbon atoms, a cycloalkyl group or an aryl group having up to 10 carbon atoms, or $R^1$ and $R^2$ may be bonded together to form a cycloalkyl group having 3 to 12 carbon atoms, each of $R^3$, $R^4$, $R^5$ and $R^6$ is independently a hydrogen atom, an alkyl group having 1 to 10 carbon atoms, a cycloalkyl group or an aryl group, and n is an integer of 0 or 1.}

[3] The method described in [1] or [2] above, wherein the allyl ether having an aromatic ring is at least one selected from the group consisting of a diallyl ether of bisphenol A, a diallyl ether of bisphenol F and 3,3',5,5'-tetramethyl-4,4'-biphenyldiol diallyl ether.

[4] The method described in any one of [1] to [3] above, wherein the viscosity of the allyl ether having an aromatic ring at 25° C. is not more than 200 mPa·s.

[5] The method described in any one of [1] to [3] above, wherein the viscosity of the allyl ether having an aromatic ring at 60° C. is not more than 100 mPa·s.

[6] The method described in any one of [1] to [5] above, wherein the total number of carbon atoms of the alkyl groups bonded to the nitrogen atom of the tertiary amine is not less than 12 and is not more than 30.

[7] The method described in any one of [1] to [5] above, wherein the total number of carbon atoms of the alkyl groups bonded to the nitrogen atom of the tertiary amine is not less than 6 and is not more than 50, and the total number of carbon atoms of the alkyl groups bonded to the nitrogen atom of the quaternary ammonium salt is not less than 7 and is not more than 80.

[8] The method described in any one of [1] to [7] above, wherein a mineral acid is further used as a catalyst.

[9] The method described in any one of [1] to [7] above, wherein a tungsten compound, a tertiary amine and a mineral acid are used as a catalyst.

[10] The method described in [9] above, wherein the total number of carbon atoms of the alkyl groups bonded to the nitrogen atom of the tertiary amine is not less than 12 and is not more than 30, and the mineral acid is sulfuric acid and/or phosphoric acid.

[11] The method described in any one of [1] to [10] above, wherein an α-aminoalkylphosphonic acid compound or an α-aminoarylphosphonic acid compound having a structure represented by the following formula (2):

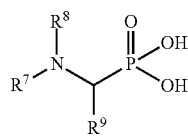

(2)

{wherein $R^7$ is a hydrogen atom or an acyl group, and each of $R^8$ and $R^9$ is independently a hydrogen atom, an alkyl group having 1 to 18 carbon atoms, or an aryl group} is further used as a cocatalyst.

Effects of the Invention

According to the method of producing an epoxy compound of the present invention, an aqueous solution of hydrogen peroxide and allyl ethers having an aromatic ring are reacted together to produce a corresponding epoxy compound by using as a catalyst a tungsten compound, and a tertiary organoamine and/or a quaternary ammonium salt, and optionally a mineral acid, without using an organic solvent as a reaction solvent. Therefore, it is made possible to produce an epoxy resin which is a useful material widely used in a variety of industrial fields, such as in the fields of electronic materials, and chemical industries, as a starting material of various polymers for adhesives, coating resins, etc., while minimizing the contamination of organic chlorine impurities, requiring simple operation, maintaining safety, in good yields and at low cost. Therefore, the method of producing an epoxy compound of the present invention offers great industrial benefits.

MODE FOR CARRYING OUT THE INVENTION

The present invention is hereinafter described in detail.
According to the method of producing an epoxy compound of the present invention, hydrogen peroxide is used as an oxidizing agent. Hydrogen peroxide can be used in the form of an aqueous solution of hydrogen peroxide. Though there is no particular limitation, the concentration of hydrogen peroxide is usually selected from a range of 1 to 80%, preferably 20 to 80%. Further, though there is no particular limitation, hydrogen peroxide is used in an amount selected from a range of 0.5 to 10 equivalents, preferably 0.8 to 2 equivalents per the carbon-carbon double bond of an allyl ether to be epoxidized.

As the tungsten compound used as a catalyst, a compound that forms a tungstic acid anion in water may be suitably used, such as tungstic acid, tungsten trioxide, tungsten trisulfide, tungsten hexachloride, phosphotungstic acid, ammonium tungstate, potassium tungstate dihydrate and sodium tungstate dihydrate. Among them, tungstic acid, tungsten trioxide, phosphotungstic acid and sodium tungstate dihydrate are particularly preferred. These tungsten compounds may be used alone or as a mixture of two or more compounds. The amount of use thereof is selected from a range of 0.0001 to 20 mol %, preferably 0.01 to 20 mol %, based on the number of carbon-carbon double bonds of the substrate olefins.

As the tertiary amine used as a catalyst, it is desirable to use a tertiary organoamine having a total number of carbon atoms of the alkyl groups bonded to the nitrogen atom thereof of not less than 6, preferably not less than 12, since an improved activity of the epoxidation reaction is attained.

The tertiary organoamine includes tributylamine, tri-n-octylamine, tri-(2-ethylhexyl)amine, N,N-dimethyllaurylamine, N,N-dimethylmyristylamine, N,N-dimethylpalmitylamine, N,N-dimethylstearylamine, N,N-dimethylbehenylamine, N,N-dimethylcocoalkylamine, N,N-dimethyltallowalkylamine, N,N-dimethyl(hydrogenated tallowalkyl)amine, N,N-dimethyloleylamine, N,N-diisopropyl-2-ethylhexylamine, N,N-dibutyl-2-ethylhexylamine, N-methyldioctylamine, N-methyldidecylamine, N-methyldicocoalkylamine, N-methyl(hydrogenated tallowalkyl)amine and N-methyldioleylamine. The total number of carbon atoms of the organoalkyl groups is preferably not more than 50, more preferably not more than 30, in view of solubility in the substrate.

As the quaternary ammonium salt, it is desirable to use a quaternary organoammonium salt in which the total number of carbon atoms of the alkyl groups bonded to the nitrogen atom thereof is not less than 7 and not more than 80, preferably not less than 13 and not more than 50, more preferably not more than 30, since an improved activity of the epoxidation reaction is attained. If the number of carbon atoms is too small, the solubility of amine in the organic phase decreases when the two-phase system of aqueous phase and organic phase is employed, and thus the reactivity decreases. If the number of carbon atoms is too large, the hydrophobic property increases, so that the solubility thereof in the substrate decreases, and thus the reactivity decreases.

Concrete examples of the quaternary ammonium salt include ammonium hydrogensulfates, such as tri-n-octylmethylammonium hydrogensulfate, trioctyl(mixture of C6 to C10)methylammonium hydrogensulfate, tri-n-octylethylammonium hydrogensulfate, tri-n-octylbutylammonium hydrogensulfate, tetra-n-octylammonium hydrogensulfate, tri(decyl)methylammonium hydrogen sulfate, tri(decyl)ethylammonium hydrogensulfate, tri(decyl)butylammonium hydrogensulfate, tetra(decyl)ammonium hydrogensulfate, tri(dodecyl)methylammonium hydrogensulfate, tri(dodecyl)ethylammonium hydrogensulfate, tri(dodecyl)butylammonium hydrogensulfate, tetra(dodecyl)ammonium hydrogensulfate, tri(tetradecyl)methylammonium hydrogensulfate, tri(tetradecyl)ethylammonium hydrogensulfate, tri(tetradecyl)butylammonium hydrogensulfate, tetra(tetradecyl)ammonium hydrogensulfate, tri(hexadecyl)methylammonium hydrogensulfate, tri(hexadecyl)ethylammonium hydrogensulfate, tri(hexadecyl)butylammonium hydrogensulfate, tetra(hexadecyl)

ammonium hydrogensulfate, tri(octadecyl)methylammonium hydrogensulfate, tri(octadecyl)ethylammonium hydrogensulfate, tri(octadecyl)butylammonium hydrogensulfate, tetra(octadecyl)ammonium hydrogensulfate, trihexylmethylammonium hydrogensulfate, trihexylethylammonium hydrogensulfate, trihexylbutylammonium hydrogensulfate, tetrahexylammonium hydrogensulfate, tetrabutylammonium hydrogensulfate, tetramethylammonium hydrogensulfate, tetraethylammonium hydrogensulfate, tetrapropylammonium hydrogensulfate, lauryldimethylbenzylammonium hydrogensulfate, benzyltrimethylammonium hydrogensulfate, benzyltriethylammonium hydrogensulfate, N-laurylpyridinium hydrogensulfate, N-cetylpyridinium hydrogensulfate and N-laurylpicolinium hydrogensulfate, as well as nitrates, sulfites, sulfates, chlorides, bromides and iodides thereof. When the quaternary organoammonium salt has too many carbon atoms, the blend thereof may be gelled. Therefore, the preferred upper limit is 50.

Further, the quaternary ammonium salt may be a nitrogen ring-containing quaternary ammonium salt. The nitrogen ring-containing quaternary ammonium salt includes quaternary ammonium salts having a nitrogen ring comprising a pyridine ring, picoline ring, quinoline ring, imidazoline ring or morpholine ring. Among them, quaternary ammonium compounds comprising a pyridine ring are preferred. Concrete examples thereof include alkyl (straight-chain or branched-chain alkyls having 8 to 20 carbon atoms, the same holds hereinafter) pyridinium salts (e.g., N-laurylpyridinium chloride, N-cetylpyridinium chloride, etc.), alkylpicolinium salts (e.g., N-laurylpicolinium chloride, etc.), alkylquinolinium chlorides, alkylisoquinolinium chlorides, alkylhydroxyethylimidazoline chlorides, alkylhydroxymorpholine chlorides and the like. Bromides, iodides, sulfates or hydrogensulfates thereof may also be used.

The tertiary amine and quaternary ammonium salt may be used alone or as a mixture of two or more compounds. The amount of use thereof is selected from a range of 0.0001 to 10 mol %, preferably 0.01 to 10 mol %, based on the number of carbon-carbon double bonds of the substrate olefins. As the catalyst, a mineral acid and/or a partly neutralized salt thereof may further be used.

It is preferable that the mineral acid used as a catalyst is at least one selected from the group consisting of phosphoric acid, sulfuric acid and boric acid. The amount of use thereof is selected so that protons of the mineral acid are in a range of 0.01 to 20 moles, preferably 0.1 to 20 moles, per mole of the carbon-carbon double bond to be epoxidized of the substrate. The partly neutralized salt of the mineral acid may be partly neutralized with an alkali metal, an alkaline earth metal or a basic compound, such as organoamine. Among these mineral acids, it is particularly desirable to use phosphoric acid, sulfuric acid or both of these acids.

In addition, as a cocatalyst, an α-aminoalkylphosphonic acid compound or an α-aminoarylphosphonic acid compound having a structure represented by the following formula (2):

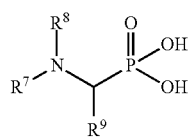

(2)

{wherein $R^7$ is a hydrogen atom or an acyl group, and each of $R^8$ and $R^9$ is independently a hydrogen atom, an alkyl group having 1 to 18 carbon atoms, or an aryl group} may be used thereby further improving the efficiency of the epoxidation reaction.

The α-aminoalkylphosphonic acid or α-aminoarylphosphonic acid can be synthesized by a method disclosed in, for example, JP-A-5-112586. In particular, the α-aminoalkylphosphonic acid and α-aminoarylphosphonic acid include α-aminomethylphosphonic acid, α-aminoethylphosphonic acid, α-aminopropylphosphonic acid, α-aminobutylphosphonic acid, α-aminopentylphosphonic acid, α-aminohexylphosphonic acid, α-aminoheptylphosphonic acid, α-aminooctylphosphonic acid, α-aminononylphosphonic acid, α-amino-α-phenylmethylphosphonic acid, N-acetyl-α-aminomethylphosphonic acid, N-propionyl-α-aminomethylphosphonic acid, N-benzoyl-α-aminomethylphosphonic acid and N-(4-methoxybenzoyl)-α-aminomethylphosphonic acid. These α-aminoalkylphosphonic acids and α-aminoarylphosphonic acids may be used alone or as a mixture of two or more compounds. The amount of use thereof is selected from a range of 0.0001 to 5 mol %, preferably 0.01 to 5 mol %, based on the number of double-double bonds of the substrate olefins.

When used as a starting material of an electronic material, it is preferable that the epoxy compound, which is a reaction product, contains less halides or sulfate ions in view of electric insulating properties. For this purpose, it is desirable to use the tertiary amine, rather than the quaternary ammonium salt, and it is preferable that the tertiary amine having 6 to 50 carbon atoms, more preferably 12 to 30 carbon atoms, is used.

When the tertiary amine is used, it is better to use the mineral acid in combination to improve the yield. As the mineral acid, sulfuric acid or phosphoric acid is preferred. When the mineral acid per se is used, the acid can be easily removed after the reaction by washing with water or an alkali aqueous solution, unlike in the case of using it as a salt in the form of a quaternary ammonium salt.

The allyl ether being the reaction substrate includes a compound having an aromatic ring and at least one allyl ether group, preferably two or more allyl ether groups. As the allyl ether, a compound represented by the following formula (1) is particularly preferred:

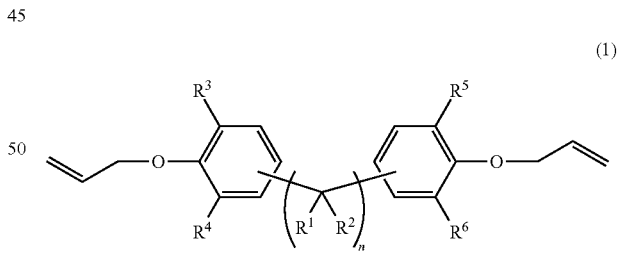

(1)

{wherein each of $R^1$ and $R^2$ is independently a hydrogen atom, an alkyl group having 1 to 6 carbon atoms, or a cycloalkyl group, or $R^1$ and $R^2$ may be bonded together to form a cycloalkane having 3 to 12 carbon atoms, each of $R^3$, $R^4$, $R^5$ and $R^6$ is independently a hydrogen atom, an alkyl group having 1 to 10 carbon atoms, a cycloalkyl group or an aryl group, and n is an integer of 0 or 1.}

The above compound includes bisphenol A diallyl ether, bisphenol F diallyl ether, 2,6,2',6'-tetramethylbisphenol A diallyl ether, 2,2'-diallylbisphenol A diallyl ether, 2,2'-di-t-butylbisphenol A diallyl ether, 2,6,2',6'-tetramethylbiphenol diallyl ether, 2,2'-diisopropylbiphenol diallyl ether, 4,4'-ethylidenebisphenol diallyl ether, 4,4'-cyclohexylidenebisphenol diallyl ether, 4,4'-(1-α-methylbenzylidene)bisphenol diallyl ether, 4,4'-(3,3,5-trimethylcyclohexylidene)bisphenol diallyl ether, 4,4'-(1-methyl-benzylidene)bisphenol diallyl ether and 3,3',5,5'-tetramethyl-4,4'-biphenyldiol diallyl ether.

It is important that these substrates are mixed with an aqueous solution of hydrogen peroxide and the catalyst without using an organic solvent, and are epoxidized. If a solvent is used, the reaction rate is very small, and depending on the solvent, an undesired reaction tends to occur, such as hydrolyzing reaction. However, if the allyl ether having an aromatic ring, which is a reaction substrate, has excessively high viscosity, the migration rate of hydrogen peroxide to the substrate is so small that it affects the reaction rate. Therefore, in order to carry out the reaction without using a solvent, the allyl ether having an aromatic ring should be in a liquid form having a viscosity which is low to a certain degree in an atmosphere of a reaction temperature. It is preferable that the viscosity at 25° C. is not greater than 200 mPa·s. The above physical value can be applied, even if it is not achieved in the form of a single compound, and for example, the mixture of a compound in the solid form at room temperature with other allyl ether group-containing compounds having an aromatic ring has a viscosity in the above range in the liquid form. Even if the substrate is in the solid form at 25° C., the substrate can be applied, for example, when it is reacted at 60° C. and its viscosity at 60° C. is not greater than 100 mPa·s.

The viscosity was measured by using the following rotary viscometer under the following conditions.
Rotary Viscometer
  Manufacturer: BROOKFIELD
  Device: DV-E VISCOMETER
  Spindle No.: 18
  Rotational speed: 50 rpm
Temperature Setting
  Constant-temperature vessel: EYELA NCB-1200 (for temperature adjustment)

From the standpoint of industrial production maintaining stability, it is desirable that the epoxidation be carried out by feeding the catalyst and the substrate into a reactor, and gradually adding the hydrogen peroxide while the consumption of the hydrogen peroxide by the reaction is being monitored, with maintaining the reaction temperature as constant as possible. In this procedure, even if the hydrogen peroxide abnormally decomposes in the reactor to generate oxygen gas, the amount of the hydrogen peroxide therein is small and an increase in the pressure can be minimized.

The excessively high reaction temperature causes side reactions, while the excessively low reaction temperature reduces the consumption rate of the hydrogen peroxide and thus the hydrogen peroxide may accumulate in the reaction system. Therefore, it is preferable that the reaction temperature is selected from a range of −10 to 120° C., preferably 40° C. to 100° C.

After the reaction was finished, there may be almost no difference in the specific gravity between the aqueous layer and the organic layer. In such a case, an aqueous solution saturated with an inorganic compound is mixed into the aqueous layer to impart a difference in the specific gravity from the organic layer to thereby separate into two layers without using an organic extraction solvent. In particular, since the tungsten compound has a large specific gravity, in order to bring the aqueous layer to the lower side, the tungsten compound may be used in an amount in excess of the above-mentioned amount which is needed as the catalyst. In this case, it is desirable to reuse the tungsten compound in the aqueous layer thereby improving the efficiency of the tungsten compound.

On the other hand, depending on the substrate, the organic layer may have a specific gravity close to 1.2. In such a case, water is added to bring the specific gravity of the aqueous layer close to 1, so that the aqueous layer is transferred to the upper layer and the organic layer is transferred the lower layer. In addition, according to the method of the present invention, the reaction is carried out without using a solvent; however, the reaction solution can be extracted by using an organic solvent, such as toluene, cyclohexane and hexane, and an optimum separation method can be selected depending on the situations.

After the organic layer separated from the aqueous layer is concentrated, the resulting epoxy compound can be obtained by a conventional method, such as distillation, chromatographic separation, recrystallization and sublimation.

EXAMPLES

The present invention is further concretely described in the Examples; however, the present invention is not limited thereto.

Example 1

0.254 Grams (1.3 mmol) of an aqueous solution containing 50% of sulfuric acid, 0.459 g (1.3 mmol) of trioctylamine, 20 g (64.8 mmol) of bisphenol A diallyl ether (viscosity at 25° C.: 50 mPa·s), 2.58 g (2.59 mmol) of sodium tungstate dihydrate and 0.144 g (1.3 mmol) of aminomethylphosphonic acid were put into a 300-mL three-neck flask equipped with a dropping funnel and Dimroth condenser, and were heated at 80° C. in an oil bath with stirring using a magnetic stirrer. Thereafter, 12.6 g (0.13 mol) of an aqueous solution containing 35% of hydrogen peroxide was added thereto dropwise in a manner that the reaction temperature did not exceed 85° C. After the addition was finished, the stirring was continued for 2 hours, and the reaction solution was cooled down to room temperature. Thereafter, 30 g of ethyl acetate was added thereto, so that the organic layer was transferred to the upper layer and the aqueous layer was transferred to the lower layer, thereby separating the organic layer.

The organic layer was analyzed to find that the conversion of bisphenol A diallyl ether was 75%, the selectivity to a monoglycidyl ether was 60% and the selectivity to a diglycidyl ether was 32%.

The conversion and the selectivity were calculated according to the following formulas based on the results analyzed by gas chromatography.

Conversion(%)=(1−mole number of the remaining starting material/mole number of the used starting material)×100

Selectivity(%)={(mole number of the object compound/mole number of the used starting material)×10000}/conversion(%)

Comparative Example 1

The reaction was carried out under the same conditions as in Example 1 except that 20 g of toluene was further added as a reaction solvent. As a result, the conversion of bisphenol A diallyl ether was 35%, the selectivity to a monoglycidyl ether was 88% and the selectivity to a diglycidyl ether was 6%.

Comparative Example 2

The reaction was carried out under the same conditions as in Example 1 except that 20 g of ethyl acetate was further added as a reaction solvent. As a result, the conversion of bisphenol A diallyl ether was 37%, the selectivity to a monoglycidyl ether was 84% and the selectivity to a diglycidyl ether was 7%.

Example 2

0.606 Grams (1.3 mmol) of methyltrioctylammonium hydrogensulfate, 0.144 g (1.30 mmol) of aminomethylphosphonic acid, 2.58 g (2.59 mmol) of sodium tungstate dihydrate and 20 g (64.8 mmol) of bisphenol A diallyl ether (viscosity at 25° C.: 50 mPa·s) were put into a 300-mL three-neck round-bottom flask equipped with a dropping funnel and Dimroth condenser. While adjusting the reaction solution to be 80° C., 12.6 g (0.13 mol) of an aqueous solution containing 35% of hydrogen peroxide was added thereto dropwise with stirring in a manner that the reaction temperature did not exceed 85° C. After the addition was finished, the stirring was continued for 2 hours, and the reaction solution was cooled down to room temperature. After the reaction was finished, 20 g of ethyl acetate was added thereto to separate the reaction solution into two layers, i.e., the organic layer transferred to the upper layer and the aqueous layer transferred to the lower layer.

The upper organic layer was analyzed to find that the conversion of bisphenol A diallyl ether was 92%, the selectivity to a monoglycidyl ether was 47% and the selectivity to a diglycidyl ether was 46%.

Example 3

20.0 Grams (60.6 mmol) of sodium tungstate was dissolved in advance in 5.95 g (30.3 mmol) of an aqueous solution containing 50% of sulfuric acid, 34 g of pure water and 5.90 g (60.7 mmol) of an aqueous solution containing 35% of hydrogen peroxide. 25.7 Grams of the aqueous solution of tungstic acid prepared above, 4.26 g (12.0 mmol) of trioctylamine (TNOA), 1.34 g (12.0 mmol) of 88% phosphoric acid and 370 g (1.2 mol) of bisphenol A diallyl ether (viscosity at 25° C.: 50 mPa·s) were put into a 2000-mL three-neck flask equipped with a dropping funnel and Dimroth condenser. While adjusting the reaction solution to be 90° C., 233 g (2.4 mol) of an aqueous solution containing 35% of hydrogen peroxide was added thereto dropwise with stirring in a manner that the reaction temperature did not exceed 95° C. After the addition was finished, the stirring was continued for 2 hours, and the reaction solution was cooled down to room temperature. After the reaction was finished, 400 g of ethyl acetate was added thereto to separate the reaction solution into two layers, i.e., the organic layer transferred to the upper layer and the aqueous layer transferred to the lower layer.

The upper organic layer was analyzed to find that the conversion of bisphenol A diallyl ether was 76%, the selectivity to a monoglycidyl ether was 56% and the selectivity to a diglycidyl ether was 35%.

Synthesis Example 1

Synthesis of a Diallyl Ether of Bisphenol F

200 Grams (0.999 mol) of bisphenol F ST (manufactured by Mitsui Chemicals, Inc.), 2.13 g (0.499 mol) of 50%-water-containing 5%-Pd/C-STD type (manufactured by N.E. CHEMCAT Corporation), 2.62 g (9.99 mmol) of triphenylphosphine (manufactured by Hokko Chemical Industry Co., Ltd.), 276 g (2.00 mol) of potassium carbonate (manufactured by Asahi Glass Co., Ltd.), 220 g (2.20 mol) of allyl acetate (manufactured by Showa Denko K.K.) and 200 g of isopropanol were put into a 2000-mL eggplant type flask, and were reacted under nitrogen atmosphere at 85° C. for 8 hours. After the reaction was finished, the reaction solution was partly sampled, diluted with ethyl acetate and analyzed by gas chromatography to determine that the ratio of bisphenol F diallyl ether to monoallyl ether was up to 99:1.

Thereafter, 400 g of toluene was added to the reaction solution, Pd/C and the precipitated solid were removed by filtration, and isopropanol and toluene were distilled off by using an evaporator. The reaction and the after-treatment were repeated four times to obtain 748 g of a distillate (isolation yield 66%, bisphenol F diallyl ether 98.7%, the remainder being monoallyl ether) and 368 g of a non-distillate (bisphenol F diallyl ether 88%) by using a molecular distillation apparatus (manufactured by Taika Kogyo Co., Ltd.). The viscosity of the distillate at 25° C. was 25 mPa·s. The ratio of the isomers was o,o'-:o,p'-:p,p'-=17:52:31.

Synthesis Example 2

Synthesis of 3,3',5,5'-tetramethyl-4,4'-biphenyldiol diallyl ether

150 Grams (0.619 mol) of 3,3',5,5'-tetramethyl-4,4'-bisphenol (manufactured by Chemical Engineering Institute, Quan-Sue Province, China), 1.32 g (0.310 mol) of 50%-water-containing 5%-Pd/C-STD type (manufactured by N.E. CHEMCAT Corporation), 1.624 g (6.19 mmol) of triphenylphosphine (manufactured by Hokko Chemical Industry Co., Ltd.), 171 g (1.24 mol) of potassium carbonate (manufactured by Nippon Soda Co., Ltd.), 136 g (1.36 mol) of allyl acetate (manufactured by Showa Denko K.K.) and 68.1 g of isopropanol were put into a 2000-mL eggplant type flask, and were reacted under nitrogen atmosphere at 85° C. for 8 hours. After the reaction was finished, the reaction solution was partly sampled, diluted with ethyl acetate and analyzed by gas chromatography to determine that the ratio of 3,3',5,5'-tetramethyl-4,4'-biphenyldiol diallyl ether to monoallyl ether was up to 97:3.

Thereafter, 200 g of toluene was added to the reaction solution, Pd/C and the precipitated solid were removed by filtration, and isopropanol and toluene were distilled off by using an evaporator. The reaction and the after-treatment were repeated four times to obtain 127.5 g of a distillate (isolation yield 66%, diallyl ether 97.9%, the remainder being monoallyl ether) and 31.7 g of a non-distillate (3,3',5,5'-tetramethyl-4,4'-biphenyldiol diallyl ether 97.5%) by using a molecular distillation apparatus (manufactured by Taika Kogyo Co., Ltd.). The distillate was a solid having a melting point of 51.7° C., and its viscosity at 60° C. was 29 mPa·s.

Example 4

0.333 Grams (0.714 mmol) of methyltrioctylammonium hydrogensulfate, 79.3 mg (0.714 mmol) of aminomethylphosphonic acid, 0.471 g (1.43 mmol) of sodium tungstate dihydrate and 20 g (71.4 mmol) of the bisphenol F diallyl ether synthesized in Synthesis Example 1 were put into a 300-mL three-neck round-bottom flask equipped with a dropping funnel and Dimroth condenser. While adjusting the reaction solution to be 80° C., 13.9 g (0.143 mol) of an aqueous solution containing 35% of hydrogen peroxide was added thereto dropwise with stirring in a manner that the reaction temperature did not exceed 85° C. After the addition was finished, the stirring was continued for 2 hours, and the reaction solution was cooled down to room temperature. After the reaction was finished, 20 g of ethyl acetate was added thereto to separate the reaction solution into two layers, i.e., the organic layer transferred to the upper layer and the aqueous layer transferred to the lower layer.

The upper organic layer was analyzed to find that the conversion of bisphenol F diallyl ether was 82%, the selectivity to a monoglycidyl ether was 56% and the selectivity to a diglycidyl ether was 34%.

Example 5

0.289 Grams (0.620 mmol) of methyltrioctylammonium hydrogensulfate, 68.9 mg (0.0620 mmol) of aminomethylphosphonic acid, 0.409 g (1.24 mmol) of sodium tungstate dihydrate and 20 g (60.2 mmol) of the 3,3',5,5'-tetramethyl-4,4'-biphenyldiol diallyl ether synthesized in Synthesis Example 2 were put into a 300-mL three-neck round-bottom flask equipped with a dropping funnel and Dimroth condenser. While adjusting the reaction solution to be 90° C., 24.1 g (0.248 mol) of an aqueous solution containing 35% of hydrogen peroxide was added thereto dropwise with stirring in a manner that the reaction temperature did not exceed 95° C. After the addition was finished, the stirring was continued for 2 hours, and the reaction solution was cooled down to room temperature. After the reaction was finished, 30 g of toluene was added thereto to separate the reaction solution into two layers, i.e., the organic layer transferred to the upper layer and the aqueous layer transferred to the lower layer.

The upper organic layer was analyzed to find that the conversion of the diallyl ether was 83%, the selectivity to a monoglycidyl ether was 61% and the selectivity to a diglycidyl ether was 34%.

INDUSTRIAL APPLICABILITY

According to the method of producing an epoxy compound of the present invention, an aqueous solution of hydrogen peroxide and allyl ethers having an aromatic ring are reacted together to produce a corresponding epoxy compound by using as a catalyst a tungsten compound, and a tertiary organoamine and/or a quaternary ammonium salt, and optionally a mineral acid, without using an organic solvent as a reaction solvent. Therefore, it is made possible to produce an epoxy resin which is a useful material widely used in a variety of industrial fields, such as the field of electronic materials, and the field of chemical industries, as a starting material of various polymers for adhesives, coating resins, etc., while minimizing the contamination of organic chlorine impurities, requiring simple operation, maintaining safety, in good yields and at low cost.

The invention claimed is:

1. A method of producing an epoxy compound by reacting an allyl ether having an aromatic ring with hydrogen peroxide to epoxidize a carbon-carbon double bond of an allyl group to thereby produce a corresponding epoxy compound having an aromatic ring, wherein water only is used as a solvent without using an organic solvent, and a tungsten compound, and a tertiary amine and/or a quaternary ammonium salt, are used as a reaction catalyst;
wherein the allyl ether having an aromatic ring is not in an organic solvent.

2. The method according to claim 1, wherein said allyl ether having an aromatic ring has a structure represented by the following formula (1):

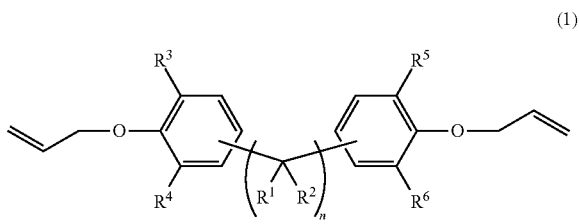

wherein each of $R^1$ and $R^2$ is independently a hydrogen atom, an alkyl group having 1 to 6 carbon atoms, a cycloalkyl group or an aryl group having up to 10 carbon atoms, or $R^1$ and $R^2$ may be bonded together to form a cycloalkyl group having 3 to 12 carbon atoms, each of $R^3$, $R^4$, $R^5$ and $R^6$ is independently a hydrogen atom, an alkyl group having 1 to 10 carbon atoms, a cycloalkyl group or an aryl group, and n is an integer of 0 or 1.

3. The method according to claim 1, wherein said allyl ether having an aromatic ring is at least one selected from the group consisting of a diallyl ether of bisphenol A, a diallyl ether of bisphenol F and 3,3',5,5'-tetramethyl-4,4'-biphenyldiol diallyl ether.

4. The method according to claim 1, wherein the viscosity of said allyl ether having an aromatic ring at 25° C. is not more than 200 mPa·s.

5. The method according to claim 1, wherein the viscosity of said allyl ether having an aromatic ring at 60° C. is not more than 100 mPa·s.

6. The method according to claim 1, wherein the total number of carbon atoms of the alkyl groups bonded to the nitrogen atom of said tertiary amine is not less than 12 and is not more than 30.

7. The method according to claim 1, wherein the total number of carbon atoms of the alkyl groups bonded to the nitrogen atom of said tertiary amine is not less than 6 and is not more than 50, and the total number of carbon atoms of the alkyl groups bonded to the nitrogen atom of said quaternary ammonium salt is not less than 7 and is not more than 80.

8. The method according to claim 1, wherein a mineral acid is further used as a catalyst.

9. The method according to claim 1, wherein a tungsten compound, a tertiary amine and a mineral acid are used as a catalyst.

10. The method according to claim 9, wherein the total number of carbon atoms of the alkyl groups bonded to the nitrogen atom of said tertiary amine is not less than 12 and is not more than 30, and said mineral acid is sulfuric acid and/or phosphoric acid.

11. A method of producing an epoxy compound by reacting an allyl ether having an aromatic ring with hydrogen peroxide to epoxidize a carbon-carbon double bond of an allyl group to thereby produce a corresponding epoxy compound having an aromatic ring, wherein water only is used as a solvent without using an organic solvent, and a tungsten compound, and a tertiary amine and/or a quaternary ammonium salt, are used as a reaction catalyst,
wherein an α-aminoalkylphosphonic acid compound or an α-aminoarylphosphonic acid compound having a structure represented by the following formula (2):

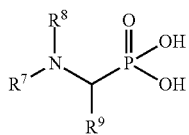

(2)

wherein R⁷ is a hydrogen atom or an acyl group, and each of R⁸ and R⁹ is independently a hydrogen atom, an alkyl group having 1 to 18 carbon atoms, or an aryl group, is further used as a cocatalyst.

12. The method according to claim 11, wherein said allyl ether having an aromatic ring has a structure represented by the following formula (1):

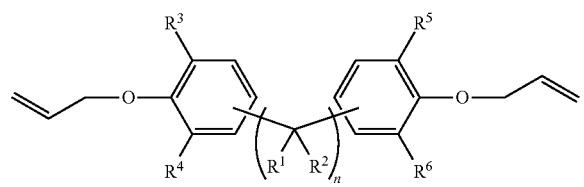

(1)

wherein each of R¹ and R² is independently a hydrogen atom, an alkyl group having 1 to 6 carbon atoms, a cycloalkyl group or an aryl group having up to 10 carbon atoms, or R¹ and R² may be bonded together to form a cycloalkyl group having 3 to 12 carbon atoms, each of R³, R⁴, R⁵ and R⁶ is independently a hydrogen atom, an alkyl group having 1 to 10 carbon atoms, a cycloalkyl group or an aryl group, and n is an integer of 0 or 1.

13. The method according to claim 11, wherein said allyl ether having an aromatic ring is at least one selected from the group consisting of a diallyl ether of bisphenol A, a diallyl ether of bisphenol F and 3,3',5,5'-tetramethyl-4,4'-biphenyl-diol diallyl ether.

14. The method according to claim 11, wherein the viscosity of said allyl ether having an aromatic ring at 25° C. is not more than 200 mPa·s.

15. The method according to claim 11, wherein the viscosity of said allyl ether having an aromatic ring at 60° C. is not more than 100 mPa·s.

16. The method according to claim 11, wherein the total number of carbon atoms of the alkyl groups bonded to the nitrogen atom of said tertiary amine is not less than 12 and is not more than 30.

17. The method according to claim 11, wherein the total number of carbon atoms of the alkyl groups bonded to the nitrogen atom of said tertiary amine is not less than 6 and is not more than 50, and the total number of carbon atoms of the alkyl groups bonded to the nitrogen atom of said quaternary ammonium salt is not less than 7 and is not more than 80.

18. The method according to claim 11, wherein a mineral acid is further used as a catalyst.

19. The method according to claim 11, wherein a tungsten compound, a tertiary amine and a mineral acid are used as a catalyst.

20. The method according to claim 19, wherein the total number of carbon atoms of the alkyl groups bonded to the nitrogen atom of said tertiary amine is not less than 12 and is not more than 30, and said mineral acid is sulfuric acid and/or phosphoric acid.

21. The method according to claim 1, wherein hydrogen peroxide is used in an amount of 1 to 2 equivalents per the carbon-carbon double bond of the allyl ether having an aromatic ring.

* * * * *